(12) United States Patent
Neuberger

(10) Patent No.: US 11,129,676 B2
(45) Date of Patent: Sep. 28, 2021

(54) DEVICE AND METHOD FOR VESSEL TREATMENT

(75) Inventor: Wolfgang Neuberger, Dubai (AE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 3 days.

(21) Appl. No.: 13/574,476

(22) PCT Filed: Jan. 20, 2011

(86) PCT No.: PCT/US2011/021801
§ 371 (c)(1),
(2), (4) Date: Jul. 20, 2012

(87) PCT Pub. No.: WO2011/091102
PCT Pub. Date: Jul. 28, 2011

(65) Prior Publication Data
US 2012/0289950 A1 Nov. 15, 2012

Related U.S. Application Data

(60) Provisional application No. 61/296,730, filed on Jan. 20, 2010.

(51) Int. Cl.
*A61B 18/22* (2006.01)
*A61B 18/00* (2006.01)
(Continued)

(52) U.S. Cl.
CPC .... *A61B 18/22* (2013.01); *A61B 2018/00202* (2013.01); *A61B 2018/00345* (2013.01);
(Continued)

(58) Field of Classification Search
CPC ....... A61B 18/24; A61B 18/22; A61B 18/245; A61B 2018/00202; A61B 2018/00345;
(Continued)

(56) References Cited

U.S. PATENT DOCUMENTS

| | | | | |
|---|---|---|---|---|
| 5,250,045 A | * | 10/1993 | Bohley | A61B 18/24 |
| | | | | 606/7 |
| 5,416,878 A | * | 5/1995 | Bruce | A61B 18/24 |
| | | | | 128/897 |

(Continued)

OTHER PUBLICATIONS

Definition of spiral. Merriam-Webster Dictionary, retrieved on Oct. 27, 2015; Retrieved from the Internet: <http://www.merriam-webster.com/dictionary/spiral>.*

(Continued)

*Primary Examiner* — Gary Jackson
*Assistant Examiner* — Sebastian X Lukjan
(74) *Attorney, Agent, or Firm* — Bolesh J. Skutnik; BJ Associates

(57) ABSTRACT

An endoluminal lasing system for treating vascular disorders is disclosed. Treatment comprises an elongated member that conveys laser radiation to tissue and a motorized mechanism, through which elongated member is rotated. As motor drives, its movement spins elongated member leading to a spiral movement as physician manually moves member in a longitudinal direction. In a preferred embodiment, elongated member is an optical fiber for endoluminal vessel treatment. In another preferred embodiment optical fiber comprises an off-axis firing distal end or side-firing distal end. Optical fiber can be a radial emitting fiber. Spin velocity can be varied according to treatment needs, i.e., pathology, type of vessel, energy source, vessel diameter, etc. One advantage, spiral movement prevents adherence to vessel wall in treatments. Another advantage is that radiation is applied more uniformly along vessel wall. The vessel wall is, thus more evenly treated under most conditions. Treatment velocity and reproducibility are enhanced with this procedure, and human errors are minimized.

14 Claims, 3 Drawing Sheets

(51) Int. Cl.
*A61B 18/20* (2006.01)
*A61B 18/18* (2006.01)

(52) U.S. Cl.
CPC . *A61B 2018/1861* (2013.01); *A61B 2018/208* (2013.01); *A61B 2018/2211* (2013.01); *A61B 2018/2238* (2013.01)

(58) Field of Classification Search
CPC .... A61B 2018/2211; A61B 2018/2238; A61B 2081/208; A61B 2018/1861
USPC ...................................................... 606/15, 16
See application file for complete search history.

(56) References Cited

U.S. PATENT DOCUMENTS

| | | | | |
|---|---|---|---|---|
| 5,733,277 | A * | 3/1998 | Pallarito | 606/7 |
| 2002/0002370 | A1 * | 1/2002 | Levatter | A61B 18/245 606/15 |
| 2005/0131400 | A1 * | 6/2005 | Hennings et al. | 606/15 |
| 2005/0203496 | A1 * | 9/2005 | Ritchie | A61B 18/24 606/15 |
| 2007/0049911 | A1 * | 3/2007 | Brown | A61B 18/24 606/12 |
| 2008/0181278 | A1 * | 7/2008 | Boutoussov | A61B 18/20 372/92 |
| 2009/0270850 | A1 * | 10/2009 | Zhou et al. | 606/15 |
| 2011/0130749 | A1 * | 6/2011 | Arcus Villacampa | A61B 18/22 606/15 |
| 2011/0144630 | A1 * | 6/2011 | Loeb | A61B 18/22 606/16 |

OTHER PUBLICATIONS

Definition of bend. Merriam-Webster Dictionary, retrieved on Oct. 27, 2015; Retrievd from the Internet: <http://www.merriam-webster.com/dictionary/bend>.*

Definition of Vascular. Merriam-Webster Dictionary, retrieved on May 23, 2016; Retrieved from the Internet: <http://www.merriam-webster.com/dictionary/vascular>.*

* cited by examiner

DEVICE AND METHOD FOR VESSEL TREATMENT

BACKGROUND OF THE INVENTION

National Stage Filed Under 35 U.S.C. § 371

This is a national stage application and it claims priority to PCT application No. PCT/US 11/21801 filed on Jan. 20, 2011, which claims the benefit of U.S. Provisional Application Ser. No. 61/296,730 filed Jan. 20, 2010, the entire contents of each of which are hereby incorporated by reference.

1. FIELD OF THE INVENTION

The present invention relates to minimally invasive treatments and in particular, to the treatment of vascular disorders by using local energy emitting devices and a radiation conveyer.

2. INVENTION DISCLOSURE STATEMENT

The blood vessels are the part of the circulatory system that transport blood throughout the body. There are three major types of blood vessels: the arteries, which carry the blood away from the heart, the capillaries, which enable the actual exchange of water and other substances between the blood and the tissues; and the veins, which carry blood from the capillaries back towards the heart.

Arteries and veins have the same basic structure. Three distinct layers can be identified, from inside to outside: tunica intima, tunica media and tunica adventitia. The main difference between arteries and veins is the proportions in which these components are present.

In the arterial system, blood pressure is usually around 120 mmHg systolic and 80 mmHg diastolic. In contrast, pressures in the venous system are constant and rarely exceed 10 mmHg.

The venous system comprises valves, whose main function is to achieve unidirectional blood flow back to the heart. Venous valves are usually bicuspid valves, with each cusp forming a blood reservoir, which force their free surfaces together under retrograde blood pressure. As a consequence, when properly operating, retrograde blood flow is prevented, allowing only antegrade flow to the heart. A valve becomes incompetent when their cusps are unable to seal properly under retrograde pressure gradient, so retrograde blood flow occurs. When retrograde blood flow occurs, pressure increases in the lower venous sections, dilating veins and usually leading to additional valvular failure.

Valvular failure, usually referred to as venous insufficiency, is a chronic disease that can lead to skin discoloration, varicose veins, pain, swelling and ulcerations. Varicose veins refer to blood vessels that have become enlarged and twisted and have progressively lost their wall elasticity. Due to the widening of the blood vessels, vein valves cannot be completely closed and veins lose their ability to carry blood back to the heart. This leads to an accumulation of blood inside the vessels, enlarging and twisting the veins even more. Furthermore, varicose veins usually have a blue or purple color and may protrude twisted above the surface of the skin, this being responsible for their characteristically unattractive appearance. They are commonly formed in the superficial veins of the legs, which are subject to high pressure when standing. Other types of varicose veins include venous lakes, reticular veins and telangiectasias. A special case of venous insufficiency may occur in arterio-venous fistula: a connection between an artery and a vein. These can be congenital, surgically created or acquired due to pathologic process. A fistula may be surgically created for hemodialysis treatments (vascular access). Arteriovenous fistula for vascular access is carried out previous to hemodialysis treatment, in order to render a larger and stronger vein for easy access to the blood system. As a consequence, an adequate vascular access is achieved, through which blood is withdrawn, purified, and returned to the body. Vascular accesses are thus entranceways into the bloodstream that lie completely beneath the skin. It is well known that vascular accesses have a high incidence of complications, finally determining vascular access failure. These can be divided into non-thrombotic and thrombotic complications, finally determining vascular access failure. Regarding non-thrombotic complications, venous hypertension is one of the most important since it may cause valvular incompetence or central venous stenosis. This may lead to severe upper limb edema, skin discoloration, access dysfunction and peripheral ischemia with resultant fingertip ulceration.

There are a number of treatments available intending to cure these kinds of vascular pathologies. Some of them only consist in relief of symptoms but they do not treat varicose veins nor prevent them from forming. These include elevating the legs by lying down or using a footstool when sitting, elastic stockings and exercise.

Varicose veins are frequently treated by eliminating the insufficient veins. This forces the blood to flow through the remaining healthy veins. Various methods can be used to eliminate the problem of insufficient veins, including, sclerotherapy, surgery (vein stripping), electro-cautery, and laser treatments.

Laser treatments are usually preferred by those skilled in the art. Minimally invasive laser surgery has been improved due to new diode laser systems. In endovascular laser surgery, laser radiation applies thermal energy to the vein via an optical fiber, and while fiber is withdrawn, the vein closes and, ideally, eventually disappears through resorption. In these and other cases, endovascular laser treatment provides an effective technique for eliminating or diminishing skin and vascular problems. A well known prior art describing endovascular laser ablation procedure includes the following steps: first, a guide wire is inserted into the vein to be treated, with the help of an entry needle. Second, an introducer sheath is introduced over the guide wire and advanced to a treatment site. Then, the guide wire is removed leaving the introducer sheath in place. The optical fiber (coupled to a laser source) is inserted through the introducer sheath and positioned so that the emitting end at the distal tip of the fiber and the sheath are at the same point. Tumescent anesthesia is then applied to the tissue surrounding the vein to be treated. Prior to lasing, the sheath is pulled back from the emitting end a distance sufficient to prevent the emitted laser energy from damaging the sheath. Then, laser is fired to emit laser radiation into the blood and/or vein wall directly in front of the emitting face. Finally, while laser energy is emitted, optical fiber and introducer sheath are withdrawn together to treat and close a desired length of the vein. Laser energy is absorbed by the blood and/or vein wall tissue. As a consequence, vein is thermally damaged, thus leading to fibrosis of the vein, which is resorbed alter some time.

From previously described laser ablation technique it can be seen that laser irradiation is fired once optical fiber is inserted inside the vein and placed in the desired position inside it. However, optical fiber seldom remains centered inside the vein while irradiation is being performed, due to the vein morphology variation along its length when fiber is displaced longitudinally. Some approaches have been proposed in order to maintain fiber centered while withdrawing. For example, U.S. Pat. No. 7,273,478 B2 describes an endoluminal catheter with a spacer design for achieving fiber centering. This kind of approaches, even when efficient, adds complexity to laser probes. In addition, it often increases probe's diameter and some designs may not fit into vein and/or may damage tissue. Furthermore, it is well known that morphology variation is usually increased in varicose veins due to their tortuosity, usually leading to failure of the approaches described in related patents. Inability to keep the optical fiber centered may lead to inefficient treatments and/or post-surgery complications. In the first case, vein closure may be incomplete thus leading to recurrent varicose veins. In the second case, a non-centered fiber may irradiate vein unevenly and cause vein wall perforation in those regions of high energy deposition, thus causing hemorrhages. Moreover, perivenous tissue damage is more likely to occur when uneven irradiation is applied. As a consequence, nerves may be damaged and patient's recovery delayed.

Recently, due to improvements in endovenous laser ablation devices and techniques, some of these drawbacks have been overcome. patent application Ser. No. 12/395,455 by Neuberger, discloses substantial improvements in optical fiber, including a rounded tip configuration and emission of radiation radially with respect to its main axis (radial fiber). As a consequence, guide wire and tumescent anesthesia would be no longer required when carrying out endovascular laser treatment. The need of tumescent anesthesia is further reduced by the usage of wavelengths that are highly absorbed in the components surrounding fiber tip, for example, 1470 nm. As a consequence, thermal effect caused in tissue by laser radiation is restricted to the zone of interest, thus preventing from damaging non-target tissue (e.g., nerves are not affected by thermal effects, thus rendering a virtually painless procedure).

As previously mentioned, optical fiber is usually withdrawn as the insufficient vein is being irradiated, in order to cause obliteration along its length. This pullback movement can be carried out manually or by using an automatic system. An example of the second case is described in U.S. Pat. No. 7,524,316 B2 by Hennings et al., in which a motorized pullback is described. In spite of technique's mentioned advantages, experience has shown that in practice a smooth pullback movement is not achieved, due to the adherence that occurs between the vein wall and the laser probe's emitting end. This undesired "sticky vein effect", may cause the vein to tear apart. In addition, vein carbonization can occur in those vein wall spots receiving excessive laser energy. When this happens, energy deposition is non-uniform and incomplete vein closure is likely to occur.

According to the previously mentioned, improvements may be carried out with respect to current vein treatments in order to enhance outcomes and render an easier and more efficient procedure.

Arteries, too, are affected by numerous pathologies. Among the most important are the congenital anomalies. One of the most important is the aneurysm: an abnormal widening or ballooning of a portion of an artery due to congenital weakness in its wall. Aneurysms are most prominent and significant in the abdominal aortic artery, intracranial arteries (supplying blood to the brain), and the aorta, but also occur in peripheral vessels such as in the popliteal arteries, femoral arteries, carotid arteries, and in arteries feeding arms and kidneys. Although it is still not exactly clear what causes aneurysms, high blood pressure and high cholesterol may raise occurrence risk of some types of aneurysms. The main complications of aneurysm include: compression of nearby structures such as nerves, infection and rupture, which can cause massive bleeding that may lead eventually to death. Furthermore, thrombi may form in the dilated pouch giving rise to emboli that may obstruct smaller vessels. In some cases, the aneurysm may dissect into the wall of an artery, blocking some of the branches.

Invasive treatments of aneurysms are either endovascular techniques (angioplasty with stent) or open surgery techniques. Open techniques include exclusion and excision.

For aneurysms in the aorta, arms, legs, or head, the weakened section of the vessel may be replaced by a bypass graft that is sutured at the vascular stumps.

Endovascular treatments are less invasive and involve insertion of a catheter into the femoral artery in the patient's leg and navigating it through the vascular system, into the aneurysm. Thermal sources have been used for treating aneurysms. For instance, U.S. Pat. No. 4,735,201 by O'Reilly discloses an optical fiber with detachable metallic tip affixed to laser energy transmitting optical fiber by hot-melt adhesive. Metallic tip serves to generate heat by absorption of laser energy for cauterization of tissue surrounding the neck of an aneurysm or other vascular opening to be occluded. The device is used for intravascular laser coagulation of arteries, veins, aneurysms, vascular malformations and arteriovenous fistulas. The heat generating tip of the device is positioned intravascularly within the neck of the aneurysm or other vascular opening to be occluded and laser energy is transmitted through the optical fiber to heat the tip and thereby coagulate the tissue surrounding the tip. As another example, U.S. Pat. No. 5,405,322, by Lennox, discloses an apparatus and method for treating an aneurysm in a vessel that isolates and evacuates volume around aneurysm site by application of RF heating, via spaced electrodes and one or more inflatable balloons within catheter. An apparatus and method for treating an aneurysm in a vessel that isolates a volume around the aneurysm, evacuates that volume and heats the aneurismal wall are disclosed. A catheter includes one or more inflatable balloons for defining the isolated volume and occluding and preventing any blood flow through the volume. When the treatment is completed, the balloons are deflated and the catheter is removed from the vessel. Thermal sources present many disadvantages. First, as heat is an unspecific source of energy, treatment precision may be compromised. Second, some studies suggest that risk of thrombosis may be significant with this kind of treatments. Third, recurrence is likely to occur after some time. Finally, these thermal methods require permanent contact between heated tip and the vessel wall for them to be effective and thus energy is delivered to the vein wall essentially only through such points of contact. Specifically regarding to RF, some drawbacks can also be mentioned. RF methods can be more time consuming and thus more stressful to the patient than otherwise desired. Moreover, the catheters used and RF electrodes are relatively complex and more expensive to manufacture than those developed for other treatment methods (e.g. laser procedures). Need for evacuation of blood in the treatment site also complicates the system and method, providing additional aspects where failure can occur.

As previously detailed, numerous approaches based on the application of laser energy have been proposed for the treatment of vein and artery pathologies. These approaches present several drawbacks. For instance, in most of prior art, optical fiber doesn't remain centered inside the vein while irradiation is being performed. Approaches trying to address this drawback usually fail due to varicose vein increased tortuosity. Furthermore, even when efficient, they add complexity to laser probes and often increase tissue damage risk due to probe's greater diameter. Inability to keep the optical fiber centered may lead to inefficient treatments (recurrent varicose veins) and/or post-surgery complications (wall perforation). Optical fiber is withdrawn while irradiating insufficient vein, in order to cause obliteration along its length. This pullback movement can be carried out manually or by using an automatic system. Experience has shown that in practice, a smooth motorized pullback movement is seldom achieved, due to the adherence that occurs between the vein wall and the laser probe's emitting end. This undesired "sticky vein effect", may cause the vein to tear apart. In addition, vein carbonization can occur in those vein wall spots receiving excessive laser energy. When this happens, energy deposition is non-uniform and incomplete vein closure is likely to occur.

There is thus a need for a minimally invasive vascular treatment that improves on the state of the art, assuring an even irradiation inside the vessel and improving pullback movement, to enhance safety and efficiency, while reducing procedure time. The present invention addresses these needs.

OBJECTIVES AND BRIEF SUMMARY OF THE INVENTION

It is an objective of the present invention to provide a device and method for improved vascular treatment of vessel disorders.

It is another objective of the present invention to treat dysfunctional vessels accurately and precisely, by using a localized, directed energy source and a radiation conveyer.

It is also an objective of the present invention to provide a device and method for safer, painless and more reliable vascular treatment by using an effective spiral radiation pattern, which guarantees a uniform delivery of energy to tissue.

It is yet another objective of the present invention to provide a device and method for preventing a radiation conveyer from adhering to vessel wall by rotational movements, facilitating its longitudinal displacement, thus leading to an improved vascular treatment.

Briefly stated, an endoluminal lasing system for treating vascular disorders is disclosed. Treatment device comprises an elongated member that conveys laser radiation to tissue and a motorized mechanism, through which elongated member is rotated. As the motor is driven, its movement spins elongated member thus leading to a spiral movement as physician manually moves member in a longitudinal direction. In a preferred embodiment, elongated member is an optical fiber for endoluminal vessel treatment. In another preferred embodiment optical fiber comprises an off-axis firing end or side-firing distal end. In another preferred embodiment, optical fiber is a radial emitting fiber or a direct emitting fiber. Spin velocity can be regulated according to treatment needs, i.e., pathology, type of vessel, energy source, vessel diameter, etc. One advantage of this invention is that spiral movement prevents adherence of elongated member to vessel wall in various treatment situations, such as when vessel shrinks due to absorption of radiation energy. Another advantage of spiral movement is that radiation is applied more uniformly along vessel wall, regardless of its tortuosity or elongated member's offset from longitudinal axis. As a consequence, the vessel wall is more evenly treated in spite of its radius and/or fiber position variation. Treatment velocity, as well as its reproducibility, is enhanced with this procedure, and human errors are highly minimized. Other medical treatments involving treatment of non-hollow tissue structures can benefit from this device, including but not limited to treatment of enlarged prostates, fat removal or firming of tissue applications.

The above and other objects, features and advantages of the present invention will become apparent from the following description read in conjunction with the accompanying drawings (in which like reference numbers in different drawings designate the same elements).

DETAILED DESCRIPTION OF PREFERRED EMBODIMENTS

The present invention addresses prior art disadvantages by assuring a uniform irradiation inside the vessel and an improved axial movement, to enhance safety and efficiency, while reducing procedure time. Axial movement is improved by using a rotating irradiation system. Therefore, adherence between vessel wall and probe's distal end is prevented through this rotational movement of the radiation delivery member, in some applications, such as endoluminal treatment of insufficient veins, such rotational movement is preferably carried out while irradiating insufficient vein during removal so as to cause complete closure of vessel. Other applications where the goal is to strengthen but not completely close a tubular structure, for example in treatment of aneurysms, rotation may be required during introduction.

Figure 1A:
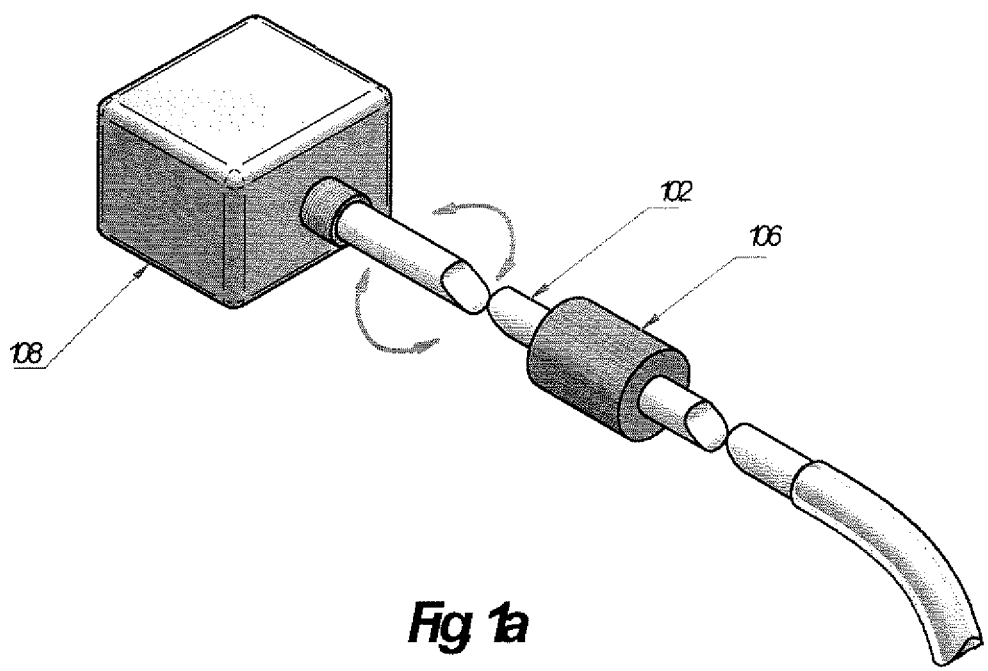
FIGS. 1a and 1b depict a preferred embodiment of present invention describing main components of the system disclosed.
Figure 1B:
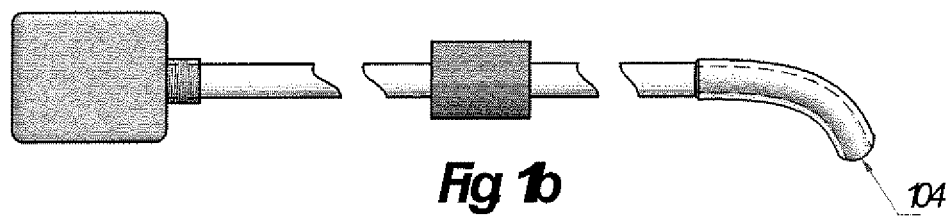

In a preferred embodiment, depicted in FIGS. 1a and 1b, optical fiber 102 comprising off-axis firing end 104 is attached to rotation drive system 108. Off-axis firing end fiber is described in U.S. patent application Ser. No. 12/714, 155 by Neuberger, and is commonly referred to as "twister fiber". Optical fiber's firing end 104 emits radiation close to vessel wall. Studies suggest that highly efficient procedures are accomplished when laser energy is applied near or contacting vessel wall in a controlled manner. The method disclosed in the present invention consists in inserting optical fiber 102 endoluminally into a vessel with the help of an entry needle. Then, under echographic guidance or by direct vision of aiming beam through skin, optical fiber is advanced to treatment site. Optical fiber 102 is coupled to rotation drive system 108, which is connected to laser source (not shown). Radiation from laser source is coupled to rotation drive system 108 by using appropriate lenses that allow an efficient electromagnetic radiation transmission between a static system and a rotational system (spinning fiber). Afterwards, laser is fired to emit electromagnetic radiation into vessel wall directly in front of the emitting face 104. While laser energy is emitted, optical fiber 102 is withdrawn to treat and close a desired length of the vein. Grip 106 is provided to facilitate manual pullback. While pulling optical fiber 102 back, it is rotated with an appropriate speed by rotation drive system 108, providing an additional benefit preventing adherence, thus, of optical fiber 102 to vessel wall. By avoiding adherence, a smooth withdrawal movement is accomplished, thus increasing precision of laser energy deposition on vessel's surface. As a consequence, various treatment situations, e.g. vessel shrinkage due to laser radiation absorption, are managed successfully with this procedure. Spinning movement is performed according to treatment needs and describes a spiral radiation pattern inside the vessel when combined with withdrawal movement. Another advantage of spiral movement is that radiation is applied uniformly along vessel wall, regardless of its tortuosity or elongated member centering. The procedure is thus safer, as there is considerably less risk of vein perforation and damage to surrounding tissue. Treatment velocity, as well as its reproducibility, is enhanced with this procedure, and human errors are highly minimized.

In another preferred embodiment, spinning velocity is regulated in real-time by rotation drive system 108, which processes feedback parameters, such as withdrawal speed. In this case, withdrawal speed is monitored in real time and used as an input to rotation drive system 108. Spinning velocity is determined by applying an appropriate algorithm based on physiological models, incorporated in the system.

In another embodiment. spinning motion in one or another direction also causes forward or backward motion respectively of fiber. Thus rotation speed and axial speed are mechanically related. This can be achieved, for example with a rotational clamp system with a thread to translate the rotating motion into a axial motion.

Figure 2:
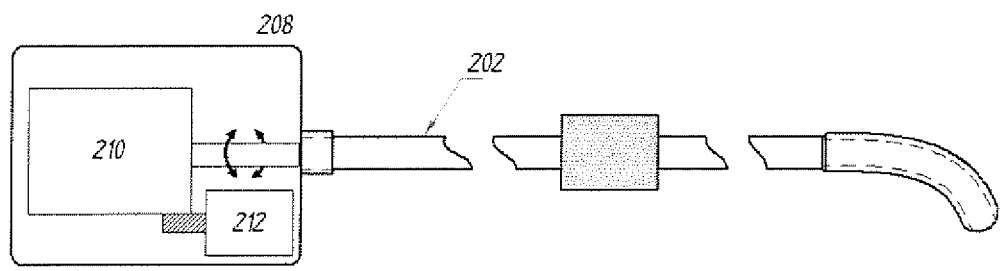
FIG. 2 shows a preferred embodiment of the present invention including an embedded laser source in the rotation drive system.

In another preferred embodiment of the present invention, depicted in FIG. 2, rotation drive system 208 also includes an embedded laser source 210. Laser source 210 is rotated by spinning driver 212. As a consequence, a complete treatment system is provided in a single device. This is possible to accomplish thanks to the reduced size of diode lasers, which allows for embedding them as a part of other systems. Therefore, laser source 210 may rotate along with spinning fiber 202 as an embedded part of rotation drive system 208, thus avoiding the use of lenses or other similar coupling mechanisms which may add complexity to the system. In another embodiment, laser source may remain static with respect to spinning fiber, thus coupling radiation from laser source to rotation drive system by an appropriate system.

Figure 3:
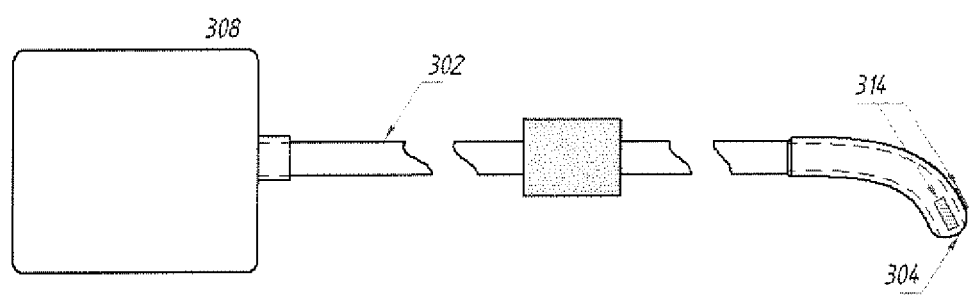
FIG. 3 depicts an embodiment in which temperature is monitored during procedure by sensors placed near optical fiber tip.

FIG. 3 shows another preferred embodiment of the present invention, in which optical spinning fiber 302 comprises temperature sensors 314 near emitting tip 304. Based on the temperature measured in the emission zone by temperature sensors 314, spinning velocity is regulated for achieving desired effect on tissue, by applying an appropriate fluency to it. Therefore, according to treatment needs, laser energy deposition in vessel wall is accomplished precisely and efficiently, thus diminishing undesired effects and complications usually caused by temperature excess. e.g. vein perforation, damage to surrounding tissue, etc. Furthermore, spinning speed may be adjusted according to withdrawal velocity (as previously explained) thus rendering a procedure regulated by two interdependent variable controls (temperature and speed of withdrawal). As a consequence, treatment reliability and safety are greatly enhanced.

Figure 4:
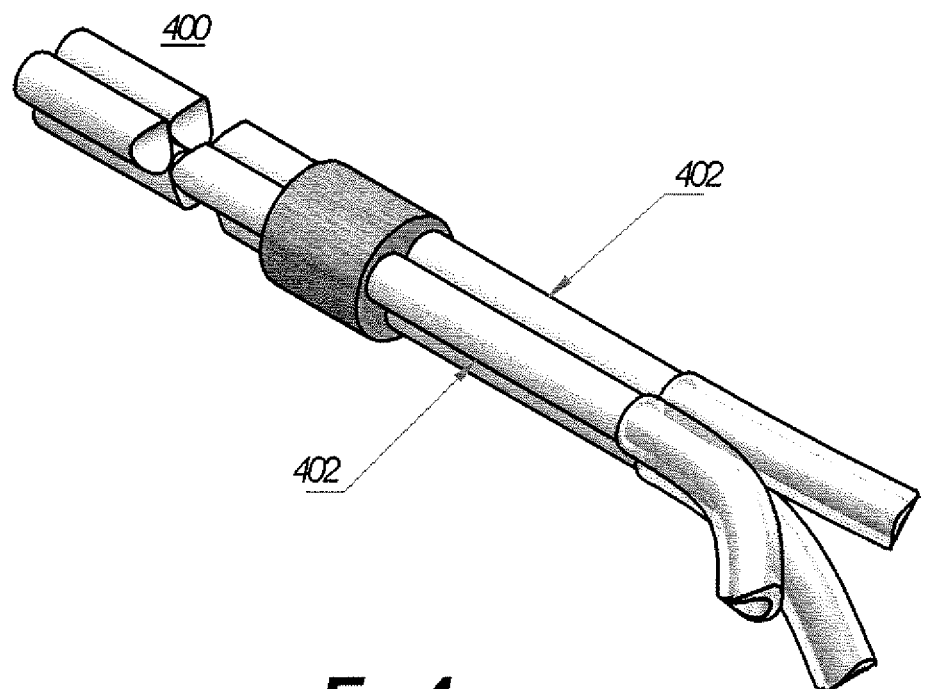
FIG. 4 shows a preferred embodiment of present invention in which a radiation conveyer includes multiple optical fibers.

In another preferred embodiment showed in FIG. 4, spinning optical fiber 400 comprises multiple off-axis firing end fibers 402. By emitting at multiple sites inside the vessel, optical fiber withdrawal speed can be increased without detriment to treatment efficiency. As a consequence, faster procedures can be performed while maintaining treatment precision.

Figure 5:
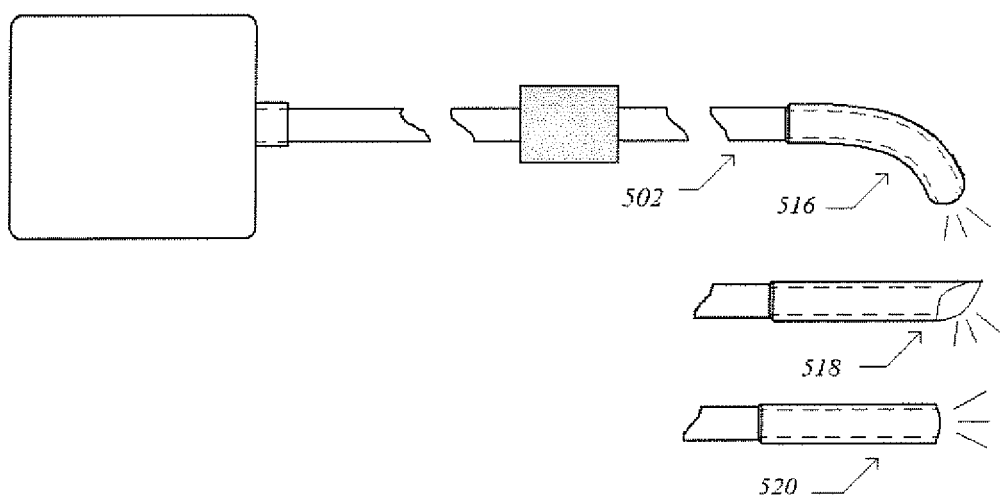
FIG. 5 depicts preferred embodiments in which different types fiber tips are used.

In other preferred embodiments, as shown in FIG. 5, optical fibers 502 with different fiber tip configurations are employed. Variants include but are not limited to off-axis tips 516, radial emitting tips 518 and direct emitting tips 520. Here again, rotational movements of fiber prevent possible adherence to vessel walls. In other preferred embodiments, optical fibers with different fiber tip configurations are employed. Variants include but are not limited to radial emitting fibers and direct emitting fibers. Here again, rotational movements of fiber prevent possible adherence to vessel walls.

In order to treat aneurysms in an efficient manner, the controlled shrinkage and strengthening of its wall structure needs to be accomplished. In a preferred embodiment of the present invention, aneurysms are treated by applying direct laser energy of appropriate wavelength and pattern thus rendering shrinkage as well as strengthening of vessel wall. A helicoidal radiation pattern is preferred and can be achieved by using a twister or side-emitting fiber, through rotational or oscillatory movements while longitudinally displacing it, thus applying energy in an even, more controlled and guided manner. It is also possible to bring the output end(s) of energy delivery devices in contact or at a controlled distance from the tissue by using spreaders, levers, balloons, spacers or other suitable tools and it is possible to use fiber optic assemblies such as fiber optic bundles.

Treatment method in this case will be similar to that previously disclosed in the embodiment regarding FIG. 1. Radiation is transported in a controlled manner via a radiation conveyer to the site where energy is needed. Radiation conveyer is inserted through the skin and inside the artery to a location nearby aneurysm in order to perform an endoluminal procedure. Once distal end of radiation conveyer is in the desired position, proximal end is connected to the rotation drive system, which in turn is connected to (or directly comprises) the energy emitting device and energy is applied to the artery wall. While applying laser energy, optical fiber is rotated or swept and displaced longitudinally. Maximum sweeping angle (to define a desired treatment area) and velocity can be set directly in the rotation drive system by the physician. As a consequence of the energy absorbed in the vessel wall, its diameter is reduced in a controlled manner, accomplishing the controlled shrinkage and strengthening of wall structure. This minimally invasive method of treating aneurysms can be used to prevent their growth at their early stages or to shrink larger ones.

In a preferred embodiment, a mini-endoscope is used to control the process by visual inspection from the inside of the vein. In addition, a real time imager such as ultrasound can be added to control the procedure. Additionally, a high resolution endovascular image can be obtained for studying the tissue to be treated in detail. For example, optical coherence tomography (OCT) imaging technology may be employed.

When laser radiation is used to apply energy to the vessel, different wavelengths can be chosen. Laser wavelength is chosen, in the present case, according to the desired penetration depth in tissue. It has been found that a wavelength that is essentially absorbed within less than a millimeter fits best the actual dimensions of the vessel wall's thickness. In a preferred embodiment, wavelength of approximately 1470±60 nm is used. Radiofrequency, microwave, thermal and other energy sources may be used to reliably and controllably perform the task and the method described, provided suitable enhancers and/or imagers as described are used. Biological additives such as growth factors or stimulants of collagen formation, for instance may be added to supplement and enhance the treatment effects by strengthening and speeding up the strengthening of the vessel structure.

In yet another preferred embodiment, specific radiation absorbers (and/or scattering enhancers) can be located at suitable positions inside the vessel wall or near the tissue to be treated, thus radiation can then selectively target tagged locations. If scatterers or absorbers are used with suitable wavelengths, energy can be transported through thicker zones. If, for instance, the absorber works at a wavelength of 980 nm, then this wavelength can also be useful for treatment. Dye molecules could be suitable absorbers or scatterers.

Although the present invention has been disclosed for treating vessels in general, it is to be understood that it is not limited thereto and may be employed to treat hollow anatomical structures in other areas of the body which may be affected by diverse pathologies.

In another preferred embodiment, non-hollow anatomical structures can be treated. For example, firming of tissue or removal of fat or other undesired tissue such as enlarged prostate tissue is rendered more efficient with present invention for several reasons. First of all, spinning system facilitates access of irradiation element to target tissue. Secondly, by spinning irradiation element while irradiating, a larger target area is reached in shorter time. Third, adherence between tissue and probe's distal end is prevented. The motion source (spinning system) that drives the spinning constitutes the means for minimizing adherence of the energy conveyer. Finally, in treatment techniques that require turning by surgeon, treatment becomes more reliable, as steadier and more constant rotation can be performed in comparison to manual rotation by surgeon.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method of treating vascular vessels in a mammal by irradiating said vessels with energy, comprising:
    Inserting directly into a vascular vessel to be treated an energy conveyer consisting of a fiber which has a proximal and a distal end, said proximal end being optically connected to an energy source and wherein said distal end has a bent tip off-axis firing end;
    positioning the bent tip off-axis firing end of the fiber so as to contact the inside wall of the vascular vessel;
    delivering energy from the energy source to inside walls of the vascular vessel through the energy conveyer; and
    rotating the energy conveyer during treatment to provide a spiral pattern of energy to the inside wall of said vascular vessel and minimize adherence of the bent tip off-axis fiber end of the fiber to said walls.

2. The method of claim 1, wherein rotating the energy conveyer comprises rotating the energy conveyer at a predetermined rotating speed, the predetermined rotating speed being associated with an axial speed of the energy conveyer and amount of energy emitted from the energy conveyer.

3. The method of claim 1, wherein rotating the energy conveyer comprises simultaneously rotating and withdrawing the energy conveyer while releasing energy to said walls.

4. The method of claim 3, wherein the energy conveyer is rotated at a predetermined rotating speed, and the predetermined rotating speed is associated with a withdrawal speed of the energy conveyer and amount of energy emitted from the energy conveyer.

5. An apparatus to treat hollow anatomical structures in mammals comprising:
    an energy source;
    an energy conveyer system consisting of a fiber, said fiber having a proximal end and a distal end, the proximal end being coupled to the energy source and the distal end having an emitting face, said emitting face being configured to contact a wall of a hollow anatomical structure during treatment; and
    a rotation source coupled to the energy conveyer system, wherein the energy conveyer system is configured to simultaneously rotate and withdraw during treatment to provide a spiral pattern of energy to the wall of the hollow anatomical structure and to minimize adherence of the emitting face of the fiber to said wall.

6. The energy conveyer system of claim 5, wherein the rotation source is coupled to the energy conveyer system at or near a proximal end thereof;
    wherein the energy conveyer system comprises a distal end where energy is emitted to a treatment site; and
    wherein the energy conveyer system is configured to rotate while being removed from a vessel, thereby minimizing adherence of the energy conveyer to a vessel wall.

7. The energy conveyer system according to claim 5 or 6, wherein said energy source is embedded onto said proximal end and in close proximity to said rotation source.

8. The apparatus according to claim 5 or 6, further comprising a rotation driver configured to regulate said rotation source, based on feedback from one or both of withdrawal speed and energy output level from said energy source.

9. The method of claim 1, wherein said distal end is positioned in said vessel proximate a treatment site.

10. A method for treating vessels in a mammal, comprising:
    inserting an energy conveyor consisting of an optical fiber having an emitting tip directly into a vessel, the emitting tip being proximate to and contacting a treatment site of the vessel; the emitting tip of the optical fiber having a bent tip off-axis firing end; and
    delivering energy to the treatment site through the optical fiber in a spiral pattern.

11. The method of claim 10, further comprising measuring a temperature around the emitting tip using a temperature sensor coupled to the energy conveyer proximate the emitting tip.

12. The method of claim 11, wherein simultaneously rotating and axially moving the energy conveyer comprises rotating the energy conveyer at a rotational speed based on the measured temperature.

13. The energy conversion system of claim 5, wherein the distal end comprises an off-axis firing end.

14. The method of claim 10, wherein the delivering the energy of the spiral pattern comprises simultaneously rotating and axially moving the energy conveyer in the vessel.

* * * * *